United States Patent
Moltzen et al.

(10) Patent No.: US 6,727,263 B2
(45) Date of Patent: Apr. 27, 2004

(54) INDOLE AND 2,3-DIHYDROINDOLE DERIVATIVES, THEIR PREPARATION AND USE

(75) Inventors: Ejner Knud Moltzen, Gentofte (DK); Jens Kristian Perregaard, Jaegerspris (DK); Ivan Mikkelsen, Koge (DK); Garrick Paul Smith, Valby (DK)

(73) Assignee: H. Lundbeck A/S, Copenhagen-Valby (DK)

(*) Notice: Subject to any disclaimer, the term of this patent is extended or adjusted under 35 U.S.C. 154(b) by 0 days.

(21) Appl. No.: 10/223,046

(22) Filed: Aug. 16, 2002

(65) Prior Publication Data

US 2003/0018050 A1 Jan. 23, 2003

Related U.S. Application Data

(62) Division of application No. 09/491,204, filed on Jan. 25, 2000, now Pat. No. 6,476,035, which is a continuation of application No. PCT/DK98/00336, filed on Jul. 20, 1998.
(60) Provisional application No. 60/053,713, filed on Jul. 25, 1997.

(30) Foreign Application Priority Data

Jul. 25, 1997 (DK) ................................................ 0892/97

(51) Int. Cl.[7] .................. A61K 31/4439; A61K 31/454; C07D 407/14; C07D 409/14
(52) U.S. Cl. .................. 514/321; 514/323; 514/338; 514/339; 546/197; 546/201; 546/277.4; 546/277.7; 546/278.1
(58) Field of Search .................. 546/197, 201, 546/277.4, 277.7, 278.1; 514/321, 323, 338, 339

(56) References Cited

U.S. PATENT DOCUMENTS

| | | | |
|---|---|---|---|
| 3,412,097 A | * 11/1968 | Corts | |
| 5,002,948 A | 3/1991 | Perregaard et al. | 514/254 |
| 5,242,925 A | 9/1993 | Boettcher et al. | 514/254 |
| 5,464,834 A | 11/1995 | Peglion et al. | 514/323 |
| 5,532,241 A | 7/1996 | Böttcher et al. | 514/254 |
| 5,693,655 A | 12/1997 | Bottcher et al. | 514/254 |

FOREIGN PATENT DOCUMENTS

| | | |
|---|---|---|
| DE | 4414113 A1 | 10/1995 |
| EP | 0376607 | 7/1990 |
| EP | 529462 | 3/1993 |
| EP | 0574313 B1 | 12/1993 |
| WO | 98/28290 | 7/1998 |
| WO | 00/43382 | * 7/2000 |

OTHER PUBLICATIONS

Grunder et al., *Psychopharmacology*, 1995, 117:472–478.
Bartoszyk et al., *European Journal of Pharmacology*, 1997, 322:147–153.

* cited by examiner

Primary Examiner—Emily Bernhardt
(74) Attorney, Agent, or Firm—Datby & Darby

(57) ABSTRACT

The present invention relates to indole and 2,3-dihydroindole derivatives having formula (I)

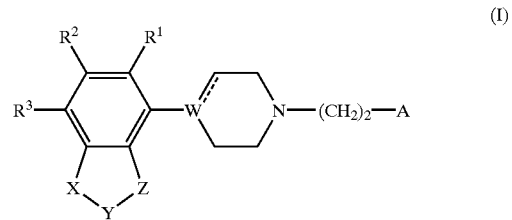

or any of its any of its enantiometers or any mixture thereof, or an acid addition salt thereof, wherein A, $R^1$, $R^2$, $R^3$, W, X, Y and Z are as described in the description. The compounds are potent serotonin reuptake inhibitors and have $5\text{-HT}_{1A}$ receptor antagonistic activity.

26 Claims, No Drawings

INDOLE AND 2,3-DIHYDROINDOLE DERIVATIVES, THEIR PREPARATION AND USE

This is a division, of application Ser. No. 09/491,204, filed Jan. 25, 2000 now U.S. Pat. No. 6,476,035 which is a continuation of International application no. PCT/DK98/00336, filed Jul. 20, 1998, which claims benefit under 35 U.S.C. §119(e) of U.S. provisional application No. 60/053,713, filed Jul. 25, 1997. Each of these prior applications is hereby incorporated herein by reference, in its entirety.

The present invention relates to novel indole and 2,3-dihydroindole derivatives which are potent serotonin reuptake inhibitors, pharmaceutical compositions containing these compounds and the use thereof for the treatment of disorders or diseases responsive to the inhibition of serotonin re-uptake. The compounds of the invention also possess antagonistic activity at 5-HT$_{1A}$ receptors and are considered to be particularly useful for the treatment of depression.

BACKGROUND

Selective serotonin (or 5-HT) reuptake inhibitors (SSRI's) such as fluoxetine, paroxetine, sertraline, fluvoxamine and citalopram represent a major step forward in the treatment of depression because they have fewer and less severe side effects compared to first generation antidepressant (tricyclics and non-selective MAO inhibitors). The side effects associated with first generation antidepressants are such that they cause some patients to withdraw from treatment.

SSRI's and all other antidepressants currently available suffer from a serious drawback in that several weeks of treatment is necessary to produce the therapeutic effect. The late onset of action is a significant problem, particularly in the treatment of patients with severe depression and suicide potential. Further, one in three patients are not responsive to SSRI's.

Electrophysiological experiments in rats have shown that acute administration of SSRIs reduces firing of 5-HT neurons of dorsal raphe nucleus in the rodent brain, whereas sustained treatment with SSRIs leads to normalization of the firing activity of the 5-HT neurons (Arborelius, L. et al, *Naunyn-Schmiedeberg's Arch. Pharmacol.* 1995, 352, 157; Gartside, S. E. et al, *Br. J. Pharmacol.* 1995, 115, 1064; Chaput, Y. et al, *Naunyn-Schmiedeberg's Arch. Pharmacol.* 1986, 33, 342).

Further, it has been shown that the recovery of the firing activity of 5-HT neurons is linked to desensitization of somatodendritic 5-HT$_{1A}$ autoreceptors (Le Poul, E. et al, *Naunyn-Schmiedeberg's Arch. Pharmacol.* 1995, 352, 141; Invernizzi, RE. et al, *Eur. J. Pharmacol.* 1994, 260, 243).

It has thus been suggested that simultaneous administration of SSRIs and an agent causing rapid desensitization or inhibition of the 5-HT$_{1A}$ receptor mediated feed back mechanism would lead to rapid onset of antidepressive effect (Artigas, F. et al, *Trends Neurosci.* 1996, 19, 378; De Vry, J., et al, *Drug News Perspec.* 1996, 9, 270)

The effect of combined administration of a compound that inhibits serotonin reuptake and a 5-HT$_{1A}$ receptor antagonist has been evaluated in several studies (Innis, R. B. et al., *Eur. J. Pharmacol.*, 1987, 143, p 195–204 and Gartside, S. E., *Br. J. Pharmacol.* 1995, 115, p 1064–1070, Blier, P. et al, *Trends Pharmacol. Sci.* 1994, 15, 220). In these studies it was found that 5-HT$_{1A}$ receptor antagonists inhibit the decrease in firing caused by acute administration of serotonin reuptake inhibitors.

Further, treatment with a combination of pindolol (a well known 5-HT$_{1A}$ receptor and β-adrenoceptor antagonist) and SSRI's has been evaluated in clinical trials. A remarkable improvement of the mood of patients was reported within one week. In addition, combined administration of pindolol and a SSRI was shown to have a good effect on patients who were non-responsive to treatment with currently available antidepressants (Artigas F. et al., *Arch. Gen. Psychiatry*, 1994, 51, p 248–251 and Blier, P. et al., *J. Clin. Psychopharmacol.* 1995, 15, p 217–222).

Several patent applications have been filed which cover the use of a combination of a 5-HT$_{1A}$ antagonist and a serotonin reuptake inhibitor for the treatment of depression (see EP-A2-687 472 and EP-A2-714 663).

In EP-A1-529 462 certain 1,4-benzodioxan derivatives having the general formula

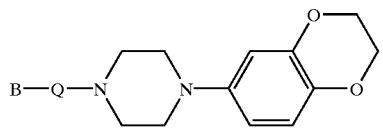

wherein B is an optionally substituted indol-3-yl group and Q is C$_n$H$_{2n}$ wherein n is 1, 2, 3, 4, 5, or 6 are disclosed. These compounds are said to have serotonin agonistic and serotonin antagonistic activity as well as serotonin reuptake inhibiting activity and to be useful as anxiolytics, antidepressants, antipsychotics, antihypertensives, and cerebroprotective agents.

In U.S. Pat. No. 5,200,948, Perregaard et al., disclose related indoles, indazoles, 2-indolones and 2,3-dihydro derivatives thereof having the formula

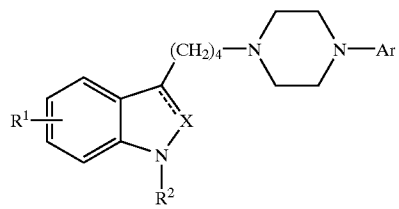

wherein X is —CH—, —CH$_2$—, —NH—, or —CO—; and Ar is

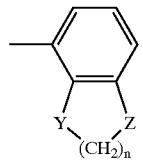

wherein Y is O, or S, Z is O, S, or —CH$_2$—, and n is 1, 2, or 3.

These compounds are valuable 5-HT$_{1A}$ receptor ligands.

OBJECT OF THE INVENTION

It is the object of the present invention to provide compounds with potent serotonin reuptake inhibiting activity as well as antagonistic properties at 5-HT$_{1A}$ receptors. Such compounds may be useful as fast onset of action medicaments for the treatment of affective disorders, such as depression.

A further object of the present invention is to provide a pharmaceutical composition comprising the above compounds as active ingredients.

SUMMARY OF THE INVENTION

The invention then, inter alia, comprises the following alone or in combination:

An indole or 2,3-dihydro-indole derivative having the formula

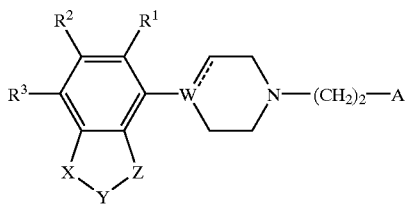

(I)

any of its enantiomers or any mixture thereof, or an acid addition salt thereof, wherein X is —O—, —S—, or —$CR^4R^5$—; and Y is —$CR^6R^7$—, —$CR^6R^7$—$CR^8R^9$—, or —$CR^6$=$CR^7$—; or X and Y together form a group —$CR^4$=$CR^5$—, or —$CR^4$=$CR^5$—$CR^6R^7$—;

Z is —O—, or —S—;

W is N, C, or CH;

A is a group selected from a group of formula (II), (III) and (IV)

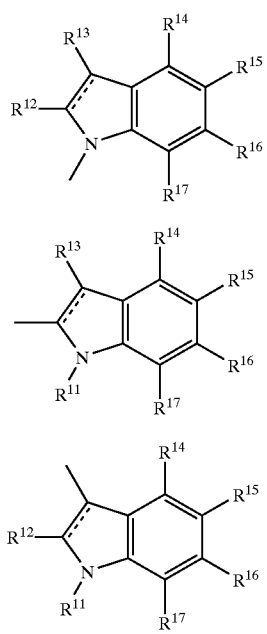

wherein the dotted lines mean an optional bond;

$R^1$, $R^2$, $R^3$, $R^{12}$, $R^{13}$, $R^{14}$, $R^{15}$, $R^{16}$ and $R^{17}$ are each independently selected from hydrogen, halogen, trifluoromethyl, alkyl, alkenyl, alkynyl, cycloalkyl, alkoxy, hydroxy, formyl, acyl, amino, alkylamino, dialkylamino, acylamino, alkoxycarbonylamino, aminocarbonylamino, alkylaminocarbonylamino, dialkylaminocarbonylamino, nitro, cyano, and aryl or arylalkyl wherein aryl may be substituted with halogen, trifluoromethyl, alkoxy, hydroxy, amino, alkylamino, nitro and cyano;

$R^4$, $R^5$, $R^6$, $R^7$, $R^8$ and $R^9$ are each independently selected from hydrogen and alkyl; and $R^{11}$ is selected from hydrogen, alkyl, alkenyl, alkynyl, cycloalkyl, aryl, arylalkyl, acyl and formyl.

In one embodiment of the invention Z is —O—, and the other substituents are as defined above.

In another embodiment of the invention Z is —S—and the other substituents are as defined above.

In a third embodiment of the invention A is a group of formula (II) and the other substituents are as defined above.

In a fourth embodiment of the invention A is a group of formula (III) and the other substituents are as defined above.

In a fifth embodiment of the invention A is a group of formula (IV) and the other substituents are as defined above.

Thus, in a special embodiment of the invention A is a group of formula (II) and Z is —O—, A is a group of formula (III) and Z is —O—, A is a group of formula (IV) and Z is —O—, A is a group of formula (II) and Z is —S—, A is a group of formula (III) and Z is —S— or A is a group of formula (IV) and Z is —S—.

In a further embodiment of the invention $R^4$, $R^5$, $R^6$, $R^7$, $R^8$ and $R^9$ are selected from hydrogen or methyl.

Examples of compounds according to the invention are

3-[2-[4-(1,4-Benzodioxan-5-yl)piperazin-1-yl]ethyl]-5-chloro-1H-indole,

3-[2-[4-(1,4-Benzodioxan-5-yl)piperazin-1-yl]ethyl]-5-bromo-1H-indole,

3-[2-[4-(1,4-Benzodioxan-5-yl)piperazin-1-yl]ethyl]-2-methyl-1H-indole,

6-Chloro-3-[2-[4-(2,2,5-trimethyl-2,3-dihydrobenzofuran-7-yl)piperidin-1-yl]ethyl]-1H-indole, 3-[2-[4-(1,4-Benzodioxan-5-yl)piperazin-1-yl]ethyl]-4-chloro-1H-indole, 6-Chloro-3-[2-[4-(2,2,-dimethyl-2,3-dihydrobenzofuran-7-yl)piperidin-1-yl]ethyl]-1H-indole, 6-Chloro-3-[2-[4-(2,2,-dimethyl-2,3,-dihydrobenzofuran-7-yl)-1,2,3,6-tetrahydro-1-pyridyl]ethyl]-1H-indole, 3-[2-[4-(1,4-Benzodioxan-5-yl)piperazin-1-yl]ethyl]-5-fluoro-1H-indole, 3-[2-[4-(1,4-Benzodioxan-5-yl)piperazin-1-yl]ethyl]-5-methoxy-1H-indole, 3-[2-[4-(1,4-Benzodioxan-5-yl)piperazin-1-yl]ethyl]-5-methyl-1H-indole, 3-[2-[4-(1,4-Benzodioxan-5-yl)piperazin-1-yl]ethyl]-6-methyl-1H-indole, 3-[2-[4-(1,4-Benzodioxan-5-yl)piperazin-1-yl]ethyl]-1H-indole, 3-[2-[4-(1,4-Benzodioxan-5-yl)piperazin-1-yl]ethyl]-6-chloro-1H-indole, 3-[2-[4-(5-Chloro-2,2-dimethyl-2,3-dihydrobenzofuran-7-yl)piperazin-1-yl]ethyl]-1H-indole, 6-Chloro-3-[2-[4-(5-chloro-3,3-dimethyl-2,3-dihydrobenzofuran-7-yl)piperazin-1-yl]ethyl]-1H-indole, 6-Chloro-3-[2-[4-(6-chloro-2,2-dimethyl-3,4-dihydro-2H-1-benzopyran-8-yl)piperazin-1-yl]ethyl]-1H-indole, 6-Chloro-3-[2-[4-(2,2-dimethyl-2,3-dihydrobenzofuran-7-yl)piperazin-1-yl]ethyl]-1H-indole, 3-[2-[4-(1,4-Benzodioxan-5-yl)piperazin-1-yl]ethyl]-4-methyl-1H-indole, 3-[2-[4-(7-Chloro-1,4-benzodioxan-5-yl)piperazin-1-yl] ethyl]-6-chloro-1H-indole, 2-[2-[4-(1,4-Benzodioxan-5-yl)piperazin-1-yl]ethyl]-6-chloro-1H-indole, 1-[2-[4-(1,4-Benzodioxan-5-yl)piperazin-1-yl]ethyl]-5-chloro-1H-indole, 3-[2-[4-(1,4-Benzodioxan-5-yl)piperazin-1-yl]ethyl]-6-chloro-2,3-dihydroindole, 6-Chloro-3-[2-[4-(2,3-dihydrobenzofuran-7-yl)piperazin-1-yl]ethyl]-1H-indole, 3-[2-[4-(1,4-Benzodioxan-5-yl)-1,2,3,6-tetrahydro-1-pyridyl]ethyl]-6-chloro-1H-indole,
3-[2-[4-(1,4-Benzodioxan-5-yl)piperidin-1-yl]ethyl]-6-chloro-1H-indole,
3-[2-[4-(1,4-Benzodioxin-5-yl)piperazin-1-yl]ethyl]-6-chloro-1H-indole,
3-[2-[4-(Benzofuran-7-yl)piperazin-1-yl]ethyl]-6-chloro-1H-indole, and
3-[2-[4-(1,3-Benzodioxolan-4-yl)piperazin-1-yl]ethyl]-6-chloro-1H-indole,
6-Chloro-3-[2-[4-(6-Chloro-1,4-benzodioxan-5-yl)piperazin-1-yl]ethyl]-1H-indole,
5-Chloro-3-[2-[4-(2,3-dihydrobenzofuran-7-yl)piperazin-1-yl]ethyl]-1H-indole,
3-[2-[4-(2,3-Dihydrobenzofuran-7-yl)piperazin-1-yl]ethyl]-5-fluoro-1H-indole,
3-[2-[4-(Benzothiophen-7-yl)piperazin-1-yl]ethyl]-5-chloro-1H-indole,
3-[2-[4-(Benzothiopyran-8-yl)piperazin-1-yl]ethyl]-5-chloro-1H-indole,
3-[2-[4-(Benzothiopyran-8-yl)piperazin-1-yl]ethyl]-5-bromo-1H-indole,
3-{2-[4-(Benzothiopyran-8-yl)piperazin-1-yl]ethyl}-6-chloro-1H-indole,
3-[2-[4-(1,4-Benzodioxan-5-yl)-1,2,3,6-tetrahydropyridin-1-yl]ethyl]-5-chloro-1H-indole,
3-[2-[4-(1,4-Benzodioxan-5-yl)-1,2,3,6-tetrahydropyridin-1-yl]ethyl]-5-fluoro-1H-indole,
3-[2-[4-(1,4-Benzodioxan-5-yl)piperidin-1-yl]ethyl]-6-chloro-1H-indole,
3-[2-[4-(1,4-Benzodioxan-5-yl)piperidin-1-yl]ethyl]-5-chloro-1H-indole,
3-[2-[4-(1,4-Benzodioxan-5-yl)piperidin-1-yl]ethyl]-5-fluoro-1H-indole,
6-Chloro-3-[2-[4-(2,3-dihydrobenzofuran-7-yl)-1,2,3,6-tetrahydropyridin-1-yl]ethyl]-1H-indole,
3-[2-[4-(Benzofuran-7-yl)-1,2,3,6-tetrahydropyridin-1-yl]ethyl]-6-chloro-1H-indole,
3-[2-[4-(Benzofuran-7-yl)-1,2,3,6-tetrahydropyridin-1-yl]ethyl]-5-bromo-1H-indole,
3-[2-[4-(Benzofuran-7-yl)-1,2,3,6-tetrahydropyridin-1-yl]ethyl]-5-fluoro-1H-indole,
3-[2-[4-(Benzofuran-7-yl)piperidin-1-yl]ethyl]-6-chloro-1H-indole,
3-[2-[4-(Benzofuran-7-yl)piperidin-1-yl]ethyl]-5-fluoro-1H-indole,
3-[2-[4-(Benzofuran-7-yl)piperidin-1-yl]ethyl]-5-bromo-1H-indole,
1-Acetyl-3-[2-[4-(1,4-benzodioxan-4-yl)piperazin-1-yl]ethyl]-2,3-dihydro-1H-indole,
1-[2-[4-(1,4-Benzodioxan-5-yl)piperazin-1-yl]ethyl]-5-fluoro-1H-indole,
1-[2-[4-(1,4-Benzodioxan-5-yl)piperazin-1-yl]ethyl]-6-chloro-1H-indole,
1-[2-[4-(1,4-Benzodioxan-5-yl)piperazin-1-yl]ethyl]-1H-indole,
1-[2-[4-(2,3-Dihydrobenzofuran-7-yl)piperazin-1-yl]ethyl]-1H-indole,
3-[2-[4-(1,4-Benzodioxan-5-yl)piperazin-1-yl]ethyl]-2,3-dihydro-1H-indole,
3-[2-[4-(1,4-Benzodioxan-5-yl)piperazin-1-yl]ethyl]-2,3-dihydro-5-fluoro-1H-indole,
3-[2-[4-(1,4-Benzodioxan-5-yl)piperazin-1-yl]ethyl]-5-chloro-2,3-dihydro-1H-indole,
3-[2-[4-(1,4-Benzodioxan-5-yl)piperazin-1-yl]ethyl]-1-butyl-1H-indole,
1-Allyl-3-[2-[4-(1,4-benzodioxan-5-yl)piperazin-1-yl]ethyl]-1H-indole,
3-[2-[4-(1,4-Benzodioxan-5-yl)piperazin-1-yl]ethyl]-1-propargyl-1H-indole,
3-[2-[4-(1,4-Benzodioxan-5-yl)piperazin-1-yl]ethyl]-2,3-dihydro-1-methyl-1H-indole,
3-[2-[4-(1,4-Benzodioxan-5-yl)piperazin-1-yl]ethyl]-1-benzyl-2,3-dihydro-1H-indole,
1-Allyl-3-[2-[4-(1,4-benzodioxan-5-yl)piperazin-1-yl]ethyl]-2,3-dihydro-1H-indole,
1-Acetyl-3-[2-[4-(1,4-benzodioxan-5-yl)piperazin-1-yl]ethyl]-1H-indole,
3-[2-[4-(Benzo-1,4-dithian-5-yl)piperazin-1-yl]ethyl]-5-chloro-1H-indole,
3-[2-[4-(Benzo-1,4-dithian-5-yl)piperazin-1-yl]ethyl]-6-chloro-1H-indole,
3-[2-[4-(Benzo-1,4-dithian-5-yl)piperazin-1-yl]ethyl]-5-fluoro-1H-indole,
3-[2-[4-(Benzo-1-thia-4-oxan-5-yl)piperazin-1-yl]ethyl]-5-chloro-1H-indole,
3-[2-[4-(Benzo-1-thia-4-oxan-5-yl)piperazin-1-yl]ethyl]-6-chloro-1H-indole, and
3-[2-[4-(Benzo-1-thia-4-oxan-5-yl)piperazin-1-yl]ethyl]-5-fluoro-1H-indole,
or an acid addition salt thereof.

The invention also relates to a pharmaceutical composition comprising a compound of formula (I) or a pharmaceutically acceptable salt thereof and at least one pharmaceutically acceptable carrier or diluent In a further embodiment, the invention relates to the use of a compound of formula (I) or a pharmaceutically acceptable acid addition salt thereof for the preparation of a medicament for the treatment of a disorder or disease responsive to the inhibition of serotonin reuptake and antagonism of 5-HT$_{1A}$ receptors.

In particular, the invention relates to the use of a compound according to the invention or a pharmaceutically acceptable acid addition salt thereof for the preparation of a medicament for the treatment of affective disorders, such as depression, psychosis, anxiety disorders including general anxiety disorder, panic disorder and obsessive compulsive disorder.

In still another embodiment, the present invention relates to a method for the treatment of a disorder or disease of living animal body, including a human, which is responsive to the inhibition of serotonin reuptake and antagonism of 5-HT$_{1A}$ receptors comprising administering to such a living animal body, including a human, a therapeutically effective amount of a compound of formula (I) or a pharmaceutically acceptable acid addition salt thereof.

In particular, the invention relates to a method for the treatment of affective disorders, such as depression, psychosis, anxiety disorders including general anxiety disorder, panic disorder and obsessive compulsive disorder comprising administering a therapeutically effective amount of a compound of formula (I) or a pharmaceutically acceptable acid addition salt thereof to a living animal body, including a human, in need thereof.

Due to their combined antagonism of 5-HT$_{1A}$ receptors and serotonin reuptake inhibiting effect, the compounds of the invention are consodered particularly useful as fast onset of action medicaments for the treatment of depression. The compounds may also be useful for the treatment of depression in patients who are resistant to treatment with currently available antidepressants.

The compounds claimed herein are considered particularly useful for the treatment of depression requiring fast onset of antidepressive effect, or a depression which is resistant to other antidepressants.

Halogen means fluoro, chloro, bromo, or iodo.

Alkyl means a straight or branched chain of one to four carbon atoms, including for example, methyl, ethyl, propyl, isopropyl and butyl.

Alkenyl means a chain of from two to four carbon atoms containing one double bond, including for example ethenyl, 1-,2-propenyl, 2-,3-propenyl etc.

Alkynyl means a chain of from two to four carbon atoms containing one triple bond, including for example ethynyl, 1-,2-propynyl, 2-,3-propynyl etc.

Cycloalkyl means cyclic alkyl of from three to seven carbon atoms, including cyclopropyl, cyclobutyl etc.

Alkoxy is —O-alkyl where alkyl is as defined above.

Acyl means —CO-alkyl wherein alkyl is as defined above.

Alkylamino means —NH-alkyl, and dialkylamino means —N—(alkyl)$_2$ where alkyl is as defined above.

Acylamino means —NH-acyl wherein acyl is as defined above.

Alkoxycarbonylamino means alkyl-O—CO—NH— wherein alkyl is as defined above.

Alkylaminocarbonylamino means alkyl-NH—CO—NH— wherein alkyl is as defined above.

Dialkylaminocarbonylamino means (alkyl)$_2$—NH—CO—NH— wherein alkyl is as defined above.

Aryl means an aromatic ring such as phenyl, or napthyl.

Arylalkyl means aryl-alkyl wherein aryl and alkyl is as defined above.

Exemplary of organic acid addition salts according to the invention are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, and theophylline acetic acids, as well as the 8-halotheophyllines, for example 8-bromotheophylline. Exemplary of inorganic acid addition salts according to the invention are those with hydrochloric, hydrobromic, sulfuric, sulfamic, phosphoric, and nitric acids. The acid addition salts of the invention are preferably pharmaceutically acceptable salts formed with non-toxic acids.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Some of the compounds of the present invention contain chiral centres and such compounds exist in the form of isomers (i.e. enantiomers). The invention includes all such isomers and any mixtures thereof including racemic mixtures.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can thus be resolved into their optical antipodes, e.g., by fractional crystallization of d- or I-(tartrates, mandelates, or camphorsulphonate) salts for example. The compounds of the present invention may also be resolved by the formation of diastereomeric derivatives.

Additional methods for the resolution of optical isomers, known to those skilled in the art, may be used. Such methods include those discussed by J. Jaques, A. Collet, and S. Wilen in "Enantiomers, Racemates, and Resolutions", John Wiley and Sons, New York (1981).

Optically active compounds can also be prepared from optically active starting materials.

The compounds of the invention can be prepared by one of the following methods comprising:

a) reducing the carbonyl groups of a compound of formula (V)

wherein $R^1$–$R^3$, $R^{12}$, $R^{14}$–$R^{17}$, X, Y, Z, W, and the dotted line are as defined above;

b) alkylating an amine of formula (VI)

wherein $R^1$–$R^3$, X, Y, Z, W, and the dotted line are as defined above with a reagent of formula G—CH$_2$CH$_2$—A wherein A is as defined above and G is a suitable leaving group such as halogen, mesylate, or tosylate;

c) reductive alkylation of an amine of formula (VI)

wherein $R^1$–$R^3$, X, Y, Z, W, and the dotted line are as defined above with a reagent of formula B—CH$_2$—A, wherein A is as defined above and B is either an aldehyde or a carboxylic acid group;

d) reducing the double bond of indoles of formula (VII)

wherein $R^1$–$R^3$, X, Y, Z, W and the dotted line are as defined above and A' is a group of formula (II), (III), or (IV) as above in which the dotted line represents a bond, in order to obtain the corresponding 2,3-dihydroindole derivatives;

e) reducing the double bond of the tetrahydropyridines of formula

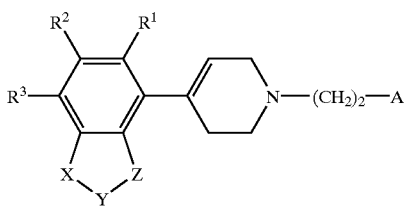

(VIII)

wherein R¹–R³, A, X, Y, and Z are as previously defined, in order to obtain the corresponding piperidine derivatives;

f) treating a compound of general formula (I) wherein Y is —CR⁶=CR⁷—, or wherein X and Y together form a group —CR⁴=CR⁵—, or —CR⁴=CR⁵—CR⁶R⁷ with a reducing agent in order to reduce the double bond, thereby obtaining a corresponding reduced ring system;

g) reductive removal of one or more of the substituents R¹–R³ or R¹²–R¹⁷ in a compound of general formula (I) in which one or more of these substituents are selected from chloro, bromo, or iodo;

h) dialkylating an amine of formula

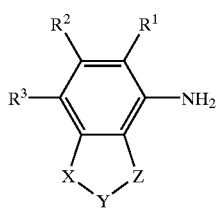

(IX)

wherein R¹–R³, X, Y and Z is as defined above with a reagent of formula

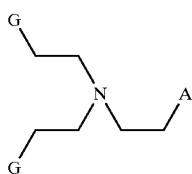

(X)

wherein A is as defined above and G is a suitable leaving group such as halogen, mesylate, or tosylate;

i) dialkylating an amine of formula

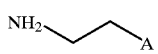

(XI)

wherein A is as defined above with a reagent of formula

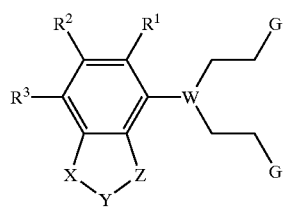

(XII)

wherein R¹–R³, X, Y, Z and W is as defined above and G is a suitable leaving group such as halogen, mesylate, or tosylate; or j) alkylating or acylating the indole nitrogen atom of compounds of formula

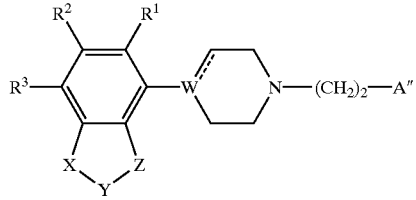

(XIII)

wherein R¹–R³, X, Y, Z, W, and the dotted line are as defined above, and A″ is a group selected from a group of formula (III), or (IV) as above in which R¹¹ is hydrogen with alkylating or acylating reagents of formula R¹¹—G, wherein G is suitable a leaving group such as halogen, mesylate, or tosylate and R¹¹ is as defined above but not hydrogen;

whereupon the compounds of formula (I) are isolated as the free base or in the form of an acid addition salt thereof.

The reduction according to method a) is preferably carried out in an inert organic solvent such as diethyl ether or tetrahydrofuran in the presence of lithium aluminium hydride at reflux temperature. Starting compounds of formula (V) are generally prepared from reagents of formula (VI), 1,3-unsubstituted indoles, and oxalyl chloride as described in the examples which follow.

The alkylation according to method b) is conveniently performed in an inert organic solvent such as a suitably boiling alcohol or ketone, preferably in the presence of a base (potassium carbonate or triethylamine) at reflux temperature.

Arylpiperazine derivatives of formula (VI) are conveniently prepared from the corresponding arylamine according to the method described by Martin et al, *J. Med. Chem.*, 1989, 32, 1052, or the method described by Kruse et al, *Rec. Trav. Chim. Pays-Bas*, 1988, 107, 303. The starting arylamines are either commercially available or are well-described in the literature.

Aryltetrahydropyridine derivatives of formula (VI) are known from literature, cf. U.S. Pat. No. 2,891,066; McElvain et al, *J. Amer. Chem. Soc.* 1959, 72, 3134. Conveniently, the corresponding arylbromide is lithiated with BuLi followed by addition of 1-benzyl-4-piperidone. Subsequent treatment with acid gives the N-benzyl-aryltetrahydropyridine. The benzyl group can be removed by catalytic hydrogenation or by treatment with e.g. ethyl chloroformate to give the corresponding ethyl carbamate followed by acidic or alkaline hydrolysis. The starting arylbromides are either commercially available or well-described in the literature.

Reagents of formula G—CH₂CH₂—A are either commercially available or can be prepared by literature methods, e.g. from the corresponding acetic acid derivative by reduction to the 2-hydroxyethyl derivative and conversion of the hydroxy group to the group G by conventional methods.

The reductive alkylation according to method c) is performed by standard literature methods. The reaction can be performed in two steps, i.e. coupling of (VI) and the reagent of formula B—CH₂—A by standard methods via the carboxylic acid chloride or by use of coupling reagents such as e.g. dicyclohexylcarbodiimide followed by reduction of the resulting amide with lithium aluminium hydride. The reaction can also be performed by a standard one-pot procedure. Carboxylic acids or aldehydes of formula B—CH₂—A are either commercially available or described in the literature.

Reduction of the indole double bond according to method d) is conveniently performed by treatment with diborane or a diborane precursor such as the trimethylamine or dimethylsulfide complex in an inert solvent such as e.g. tetrahydrofuran or dioxane from 0° C. to reflux temperature followed by acid catalyzed hydrolysis of the intermediate borane derivative. The reduction can alternatively be performed by treatment with sodium cyanoborohydride in trifluoroacetic acid.

Reduction of the double bonds according to methods e) and f) is most conveniently perfomed by hydrogenation in an alcohol in the presence of a noble metal catalyst, such as e.g. platinum or palladium.

The removal of halogen substituents according to method g) is conveniently performed by catalytic hydrogenation in an alcohol in the presence of a palladium catalyst or by treatment with ammonium formate in an alcohol at elevated temperatures in the presence of a palladium catalyst.

The dialkylation of amines according to methods h) and i) is most conveniently performed at elevated temperatures in an inert solvent such as e.g. chlorobenzene, toluene, N-methylpyrrolidone, dimethylformamide, or acetonitrile. The reaction might be performed in the presence of base such as e.g. potassium carbonate or triethylamine. Starting materials for processes h) and i) are commercially available or can be prepared from commercially available materials using conventional methods.

The N-alkylation according to method j) is performed in an inert solvent such as e.g. an alcohol or ketone at elevated temperatures in the presence of base, e.g. potassium carbonate or triethylamine at reflux temperature. Alternatively, a phase-transfer reagent can be used.

The following examples will illustrate the invention further. They are, however, not to be construed as limiting.

EXAMPLES

Halogen-, methyl-, or methoxy substituted indoles used as described in Example 1 are commercially available.

Substituted 2-(1-indolyl)acetic acids used as described in Example 3 are prepared from the corresponding substituted indole and ethyl bromoacetate by conventional methods.

Substituted 3-(2-bromoethyl)indoles used as described in Example 2 are prepared from the corresponding in 2-(1-indolyl)acetic acid ester by reduction to the alcohol with lithium aluminium hydride and subsequent treatment with tetrabromomethane/triphenylphosphine according to standard literature methods.

Arylpiperazines used as described in Examples 1, 2, and 3 are prepared from the corresponding arylamine according to the method described by Martin et al, J. Med. Chem. 32 (1989) 1052, or the method described by Kruse et al, Rec. Trav. Chim. Pays-Bas 107 (1988) 303.

The starting arylamines are either commercially available or are described in the literature as follows:

The synthesis of 5-amino-1,4-benzodioxane is described by Dauksas et al, Zh. Org. Khim. 3 (1967) 1121. The corresponding chlorinated derivatives are made in a similar manner.

The synthesis of 7-amino-2,3-dihydrobenzofuran is described in U.S. Pat. Appl. Ser. No. 4,302,592.

The synthesis of 7-amino-benzofuran is described by Van Wijngaarden et al, J. Med. Chem. 31 (1988) 1934.

The synthesis of 7-amino-benzo[b]thiophene is described by Boswell et al, J. Heterocycl. Chem. 5 (1968) 69.

7-amino-2,3-dimethylbenzofuran and the corresponding 5-chloro and 5-methyl derivatives are prepared according to Ger. Offen. DE 3526510.

4-Amino-benzothiopyran were prepared according to Eur. Pat. Appl. EP 79683.

8-Amino-6-chloro-2,2-dimethylebenzopyran was prepared by conventional nitration of 6-chloro-2,2-dimethylebenzopyran (prepared according to Bolzoni et al, Angew. Chem. 90 (1978)727-) with subsequent reduction of the obtained 8-nitro derivative. In a similar manner 7-amino-5-chloro-3,3-dimethylbenzofuran was obtained from 5-chloro-3,3-dimethylbenzofuran (prepared according to Eur. Pat. Appl. EP 7719 800206). The corresponding dechloro derivatives were obtained by treatment with hydrogen gas in the presence of a nobel metal catalyst according to standard procedures.

Aryl tetrahydropyridine derivatives are known from literature (cf. U.S. Pat. No. 2,891,066 or McElvain et al, J. Amer. Chem. Soc. 72 (1959) 3134). Most conveniently, the corresponding aryl bromide is lthiated with BuLi followed by addition of 1-benzyl-4-piperidone. Subsequent treatment with mineral acid or trifluoroacetic acid gives the N-benzyl-aryltetrahydropyridine. The benzyl group can be removes by catalytic hydrogenation or by treatment e.g. ethyl chloroformate to the corresponding ethyl carbamate followed by acidic or alkaline hydrolysis. The corresponding piperidine derivatives can be obtained by reductive removal of the double bond of the tetrahydropyridine ring. All these procedures are well-known to a person skilled in the art. The starting aryl bromides are well-described in the literature. In this manner 4-(1,4-benzodioxan-5-yl)-1,2,3,6-tetrahydropyridine, 4-(2,3-dihydro-2,2-dimethylbenzofuran-7-yl)-1,2,3,6-tetrahydropyridine, 4-(2,3-dihydrobenzofuran-7-yl)-1,2,3,6-tetrahydropyridine, 4-(benzofuran-7-yl)-1,2,3,6-tetrahydropyridine, and the corresponding piperidines were obtained.

Melting points were determined on a Buchi SMP-20 apparatus and are uncorrected. Mass spectra were obtained on a Quattro MS—MS system from VG Biotech, Fisons Instruments The MS—MS system was connected to an HP 1050 modular HPLC system. A volume of 20–50 µL of the sample (10 µg/mL) dissolved in a mixture of 1% acetic acid in acetonitrile/water 1:1 was introduced via the autosampler at a flow of 30 µL/min into the electrospray source. Spectra were obtained at two standard sets of operating conditions One set to obtain molecular weight information (MH+) (21 eV) and the other set to induce fragmentation patterns (70 eV) The background was subtracted. The relative intensities of the ions are obtained from the fragmentation pattern. When no intensity is indicated for the Molecular Ion (MH+) this ion was only present under the first set of operating conditions. 1H NMR spectra were recorded of all novel compounds at 250 MHZ on a Bruker $AC_{250}$ or at 500 MHz on a Bruker DRX 500. Deuterated chloroform (99.8% D) or dimethylsulfoxide (99.9% D) were used as solvents. TMS was used as internal reference standard. Chemical shifts are expressed as ppm values. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet. NMR signals corresponding to acidic protons are generally omitted. Content of water in crystalline compounds was determined by Karl Fischer titration. Standard workup procedures refer to extraction with the indicated organic solvent from proper aqueous solutions, drying of combined organic extracts (anhydrous $MgSO_4$ or $NaSO_4$), filtering, and evaporation of the solvent in vacuo. For column chromatography silica gel of type Kieselgel 60, 230–400 mesh ASTM was used.

Example 1

3-[2-[4-(1,4-Benzodioxan-5-yl)Piperazin-1-yl] Ethyl]-5-Chloro-1H-Indole Oxalate, 1a A solution of 5-chloroindole (5.0 g) in diethyl ether (130 mL) was cooled to 0° C. under a nitrogen atmosphere followed by dropwise addition of a solution of oxalyl chloride (4.6 g) in diethyl ether (20 mL). After stirring for 16 h, the crystalline product, 2-(5-chloro-1H-indol-3-yl)-2-oxoacetyl chloride was collected by filtration (7.2 g).

A solution of this product (2.0 g) in dry tetrahydrofuran (25 mL) was added dropwise to a mixture of 1-(1,4-benzodioxan-5-yl)piperazine (1.2 g) and triethylamine (7.5 mL) in tetrahydrofuran (75 mL) at room temperature. The mixture was stirred for 16 h followed by filtration and removal of solvent in vacuo giving crude 3-[2-[4-(1,4-benzodioxan-5-yl)piperazin-1-yl]-1,2-dioxoethyl]-5-chloro-1H-indole as a solid. This product was dissolved in tetrahydrofuran (25 mL) and added dropwise to a suspension of lithium aluminium hydride (2.1 g) in tetrahydrofuran at room temperature under a nitrogen atmosphere. After reflux for 3.5 h, the reaction was quenched with aq. sodium hydroxide followed by standard workup with ethyl acetate. The resulting oil was purified by flash chromatography (eluent: heptane/ethanol/ethyl acetate/triethylamine 15:2:2:1). The oxalate salt was obtained from an acetone solution by addition of oxalic acid and recrystallized from methanol/tetrahydrofuran (1:5) giving 0.8 g of 1a. Mp: 224–28° C. $^1$H NMR (DMSO-d$_6$): 3.05 (t, 2H); 3.10–3.50 (m, 10H); 4.15–4.30 (m, 4H); 6.50 (d, 1H); 6.55 (d, 1H); 6.75 (t, 1H); 7.10 (d, 1H); 7.30 (s, 1H); 7.40 (d, 1H); 7.65 (s, 1H); 11.15 (s, 1H). MS m/z (%): 398 (MH+, 9%), 233 (100%), 221 (29%), 218 (19%), 178 (59%).

The following compounds were prepared analogously:

3-[2-[4-(1,4-Benzodioxan-5-yl)piperazin-1-yl]ethyl]-5-bromo-1H-indole oxalate, 1b, mp 236–40° C. $^1$H NMR (DMSO-d$_6$): 3.10 (t, 2H); 3.15–3.45 (m, 10H); 4.15–4.30 (m, 4H); 6.50 (d, 1H); 6.60 (d, 1H); 6.75 (t, 1H); 7.20 (d, 1H); 7.30 (s, 1H); 7.35 (d, 1H); 7.80 (s, 1H); 11.20 (s, 1H). MS m/z (%): 444 (MH+, 5%), 442 (5%), 233 (80%), 224 (21%), 222 (22%), 221 (25%), 218 (23%), 190 (19%), 70 (100%).

3-[2-[4-(1,4-Benzodioxan-5-yl)piperazin-1-yl]ethyl]-2-methyl-1H-indole oxalate, 1c, mp 205–8° C. $^1$H NMR (DMSO-d$_6$): 2.35 (s, 3H); 2.95–3.15 (m, 4H); 3.15–3.45 (m, 8H); 4.15–4.30 (m, 4H); 6.50 (d, 1H); 6.60 (d, 1H); 6.75 (t, 1H), 6.95 (t, 1H); 7.00 (t, 1H); 7.25 (d, 1H); 7.50 (d, 1H); 10.85 (s, 1H). MS m/z (%): 378 (MH+, 5%), 233 (9%), 221 (7%), 218 (5%), 158 (100%).

6-Chloro-3-[2-[4-(2,2,5-trimethyl-2,3-dihydrobenzofuran-7-yl)piperidin-1-yl]ethyl]-1H-indole fumarate, 1d, mp 232–37° C. $^1$H NMR (DMSO-d$_6$): 1.40 (s, 6H); 1.65–1.85 (m, 4H); 2.20 (s, 3H); 2.30 (t, 2H); 2.60 (t, 2H); 2.70–2.85 (m, 3H); 2.90 (s, 3H); 3.10–3.30 (m, 2H); 6.60 (s, 2H); 6.70 (s, 1H); 6.80 (s, 1H); 7.00 (d, 1H); 7.20 (s, 1H); 7.35 (s, 1H); 7.55 (d, 1H); 10.95 (s, 1H). MS m/z (%): 423 (MH+, 11%), 258 (100%), 178 (14%), 70 (41%).

3-[2-[4-(1,4-Benzodioxan-5-yl)piperazin-1-yl]ethyl]-4-chloro-1H-indole oxalate, 1e, mp 210–18° C. $^1$H NMR (DMSO-d$_6$): 3.10–3.50 (m, 12H); 4.10–4.30 (m, 4H); 6.50 (d, 1H); 6.60 (d, 1H); 6.75 (t, 1H); 7.00 (d, 1H); 7.05 (t, 1H); 7.30–7.40 (m, 2H); 11.40 (s, 1H). MS m/z (%): 398 (MH+, 10%), 233 (100%), 221 (47%), 218 (18%), 180 (25%), 178 (84%).

6-Chloro-3-[2-[4-(2,2,-dimethyl-2,3-dihydrobenzofuran-7-yl)piperidin-1-yl]ethyl]-1H-indole oxalate, 1f, mp 190–93° C. $^1$H NMR (DMSO-d$_6$): 1.40 (s, 6H); 1.75–.195 (m, 4H), 2.50–2.70 (m, 2H); 2.70–2.80 (m, 1H); 2.85–3.05 (m, 6H); 3.25–3.40 (m, 2H); 6.75 (t, 1H); 6.95 (d, 1H); 6.95–7.10 (m, 2H); 7.25 (s, 1H); 7.40 (s, 1H); 7.55 (d, 1H); 11.00 (s, 1H).). MS m/z (%): 409 (MH+, 6%), 244 (100%), 232 (9%), 178 (16%).

6-Chloro-3-[2-[4-(2,2,-dimethyl-2,3,-dihydrohydrobenzofuran-7-yl)-1, 2,3,6-tetrahydro-1-pyridyl]ethyl]-1H-indole oxalate, 1g, mp 200–4° C. $^1$H NMR (DMSO-d$_6$): 1.40 (s, 6H); 2.70–2.80 (m, 2H); 3.00 (s, 2H); 3.15 (t, 2H); 3.30 (t, 2H); 3.35–3.50 (m, 2H); 3.85–4.00 (m, 2H); 6.35 (s, 1H); 6.85 (t, 1H); 7.00 (d, 1H); 7.05–7.15 (m, 2H); 7.30 (s, 1H); 7.40 (s, 1H); 7.60 (d, 1H); 11.15 (s, 1H). MS m/z (%): 407 (MH+, 2%), 207 (8%), 180 (33%), 178 (100%).

3-[2-[4-(1,4-Benzodioxan-5-yl)piperazin-1-yl]ethyl]-5-fluoro-1H-indole oxalate, 1h, mp 224–26° C. $^1$H NMR (DMSO-d$_6$): 3.10 (t, 2H); 3.10–3.50 (m, 10H); 4.15–4.35 (m, 4H); 6.50 (d, 1H); 6.60 (d, 1H); 6.75 (t, 1H); 6.95 (t, 1H); 7.30 (s, 1H); 7.30–7.50 (m, 2H); 11.10 (s, 1H) MS m/z (%): 382 (MH+, 9%), 233 (78%), 221 (30%), 218 (22%), 190 (20%),162 (97%), 70 (100%).

3-[2-[4-(1,4-Benzodioxan-5-yl)piperazin-1-y]ethyl]-5-methoxy-1H-indole hemioxalate, 1i, mp 189–96° C. $^1$H NMR (DMSO-d$_6$): 3.00 (t, 2H); 3.05–3.30 (m, 10H); 3.80 (s, 3H); 4.15–4.35 (m, 4H); 6.50 (d, 1H); 6.55 (d, 1H); 6.70–6.80 (m, 2H); 7.10 (s, 1H); 7.15 (s, 1H); 7.25 (d, 1H); 10.70 (s, 1H). MS m/z (%): 394 (MH+, 7%), 233 (79%), 218 (21%), 190 (21%), 174 (61%), 70 (100%).

3-[2-[4-(1,4-Benzodioxan-5-yl)piperazin-1-yl]ethyl]-5-methyl-1H-indole hemifumarate, 1j, mp 147–54° C. $^1$H NMR (DMSO-d$_6$): 2.40 (s, 3H); 2.60–2.80 (m, 6H); 2.85 (t, 2H); 2.95–3.15 (m, 4H); 4.15–4.30 (m, 4H); 6.45 (d, 1H); 6.50 (d, 1H); 6.60 (s, 1H); 6.70 (t, 1H); 6.90 (d, 1H); 7.10 (s, 1H); 7.20 (d, 1H); 7.30 (d, 1H); 10.65 (s, 1H).

3-[2-[4-(1,4-Benzodioxan-5-yl)piperazin-1-yl]ethyl]-6-methyl-1H-indole hemifumarate, 1k, mp 204–7° C. $^1$H NMR (DMSO-d$_6$): 2.35 (s, 3H); 2.60–2.80 (m, 6H); 2.90 (t, 2H); 2.95–3.15 m, 4H); 4.10–4.30 (m, 4H); 6.45 (d, 1H); 6.50 (d, 1H); 6.60 (s, 1H); 6.70 (t, 1H); 6.80 (d, 1H); 7.05 (s, 1H); 7.10 (s, 1H); 7.40 (d, 1H); 10.60 (s, 1H).

6-Chloro-3-[2-[4-(7-chloro-1,4-benzodioxan-5-yl)piperazin-1-yl]ethyl]-1H-indole oxalate, 1l, mp 237–38° C. $^1$H NMR (DMSO-d$_6$): 3.00–3.15 (m, 2H); 3.15–3.40 (m, 10H); 4.20 (s, 4H); 6.50 (d, 1H); 6.65 (d, 1H); 7.00 (dd, 1H); 7.25 (d, 1H); 7.40 (d, 1H); 7.60 (d, 1H); 10.95 (s, 1H). MS m/z (%): 432 (MH+, 3%), 267 (42%), 252 (12%), 224 (10%),178 (27%), 70 (100%).

6-Chloro-3-[2-[4-(6-Chloro-1,4-benzodioxan-5-yl)piperazin-1-yl]ethyl]-1H-indole oxalate, 1m, mp 216–17° C. $^1$H NMR (DMSO-d$_6$): 2.60 (t, ?H); 2.85 (t, 2H); 3.10 (b, 4H); 3.30 (s, 4H); 4.15–4.30 (m, 4H); 6.15 (d, 1H); 6.35 (d, 1H); 7.00 (dd, 1H); 7.20 (d, 1H); 7.35 (d, 1H); 7.55 (d, 1H); 10.95 (s, 1H). MS m/z (%): 432 (MH+, 2%), 267 (47%), 252 (16%), 224 (16%), 178 (30%), 70 (100%).

5-Chloro-3-[2-[4-(2,3-dihydrobenzofuran-7-yl)piperazin-1-yl]ethyl]-1H-indole oxalate, 1n, mp 134–38° C. $^1$H NMR (DMSO-d$_6$): 2.65–2.80 (m, 6H); 2.90 (t, 2H); 3.00–3.25 (m, 6H); 4.50 (t, 2H); 6.60 (s, 1H); 6.65 (d, 1H); 6.75 (t, 1H); 6.85 (d, 1H); 7.05 (d, 1H); 7.25 (s, 1H); 7.35 (d, 1H); 7.60 (s, 1H); 11.05 (s, 1H). MS m/z (%): 382 (MH+), 217 (39%), 205 (17%), 178 (38%), 143 (11%), 70 (100%).

6-Chloro-3-[2-[4-(2,3-dihydrobenzofuran-7-yl)piperazin-1-yl]ethyl]-1H-indole oxalate, 1o, mp 205–7° C. $^1$H NMR (DMSO-d$_6$): 2.60–2.75 (m, 6H); 2.90 (t, 2H); 3.00–3.20 (m, 6H); 4.50 (t, 2H); 6.60 (s, 1H); 6.65 (d, 1H); 6.75 (t, 1H); 6.80 (d, 1H); 6.95 (d, 1H); 7.20 (s, 1H); 7.35 (s, 1H); 7.55 (d, 1H); 10.95 (s, 1H). MS m/z (%): 382 (MH+), 217 (33%), 202 (18%) 70 (100%).

3-[2-[4-(2,3-Dihydrobenzofuran-7-yl)piperazin-1-yl]ethyl]-5-fluoro-1H-indole oxalate, 1p, mp 145–49° C. $^1$H NMR (DMSO-d$^6$): 2.65–2.85 (m, 6H); 2.90 (t, 2H);

3.00–3.20 (m, 6H); 4.50 (t, 2H); 6.60 (s, 1H); 6.65 (d, 1H); 6.75 (t, 1H); 6.85 (d, 1H); 6.90 (t, 1H); 7.25 (s, 1H); 7.25–7.35 (m, 2H); 10.95 (s, 1H). MS m/z (%): 366 (MH+, 4%), 217 (31%), 205 (18%), 174 (16%), 162 (81%) 70 (100%).

3-[2-[4-(Benzothiophen-7-yl)piperazin-1-yl]ethyl]-5-chloro-1H-indole, oxalate, 1 q, mp 175.2–176.6° C. $^1$H NMR (DMSO-$d_6$): 3.10 (m, 2H), 3.26 (m, 2H), 3.38–3.36 (m, 6H), 7.05 (d, 1H), 7.09 (d, 1H), 7.33 (s, 1H), 7.40–7.37 (m, 3H), 7.47 (d, 1H), 7.62 (d, 1H), 7.69 (s, 1H), 7.76 (d, 1H). MS m/z 398.1 (MH+, 1.1% ($^{37}$Cl)), 396.1 (MH+, 2.8% ($^{35}$Cl)), 230.9 (1005), 177.8 (58%), 69.8 (50.8%).

3-[2-[4-(Benzothiopyran-8-yl)piperazin-1-yl]ethyl]-5-chloro-1H-indole, 1r, mp 152–153° C. $^1$H NMR (CDCl$_3$): 2.08 (m, 2H), 2.75 (m, 6H), 2.83 (m, 2H), 2.98 (m, 4H), 3.05 (m, 2H), 6.80 (d, 1H), 6.99–6.94 (m, 2H), 7.08 (s, 1H), 7.14 (d, 2H), 7.26 (d, 1H), 7.59 (s, 1H), 8.00 (s, 1H). MS m/z 412.3 (MH+, 100% ($^{35}$Cl)), 414.5 (MH+, 63. % ($^{37}$Cl)), 247.1 (23.7%).

3-[2-[4-(Benzothiopyran-8-yl)piperazin-1-yl]ethyl]-5-bromo-1H-indole, 1s, mp 166–167 ° C. $^1$H NMR (CDCl$_3$): 2.04 (m, 2H), 2.75 (m, 6H), 2.82 (m, 2H), 2.98 (m, 4H), 3.05 (m, 4H), 6.81 (d, 1H), 6.98–6.93 (m, 2H), 7.05 (s, 1H), 7.21 (d, 1H), 7.26 (d, 1H), 7.76 (s, 1H), 8.02 (s, 1H). MS m/z458.4 (MH+, 21.7% ($^{81}$Br), 456.3 (MH+, 23.9% ($^{79}$Br), 232.0 (58.7%), 143.1 (100%)

3-[2-[4-(Benzothiopyran-8-yl)piperazin-1-yl]ethyl]-6-chloro-1H-indole, 1t, mp 178–179° C. $^1$H NMR (CDCl$_3$) :2.07 (m, 2H), 2.75 (m, 6H), 2.83 (m, 2H), 2.98 (m, 4H), 3.04 (m, 4H), 6.80 (d, 1H), 6.98–6.92 (m, 2H), 7.04 (s, 1H), 7.08 (d, 1H), 7.33 (s, 1H), 7.52 (d, 1H), 7.95 (s, 1H). MS m/z 412.3 (MH+, 31.8% ($^{35}$Cl)), 247.3 (81.8%), 232.0 (63.9%), 178.1 (63.6%),143.1 (100%).

3-[2-[4-(Benzofuran-7-yl)piperazin-1-yl]ethyl]-6-chloro-1H-indole, 1u, mp 202–4° C. $^1$H NMR (DMSO-$d_6$): 2.65–2.85 (m, 6H); 2.90 (t, 2H); 3.20–3.40 (m, 4H); 6.60 (s, 1H); 6.80 (d, 1H); 6.90 (d,1H); 7.00 (d, 1H); 7.05–7.30 (m, 3H); 7.40 (d, 1H); 7.55 (d, 1H); 7.95 (d,1H); 11.00 (s, 1H). MS m/z (%): 380 (MH+, 4%), 215 (100%), 200 (12%), 178 (36%), 172 (20%).

3-[2-[4-(1,4-Benzodioxan-5-yl)-1,2,3,6-tetrahydropyridin-1-yl]ethyl]-6-chloro-1H-indole oxalate, 1v, mp 240–47° C. $^1$H NMR (DMSO-$d_6$): 2.70 (s, 2H); 3.10 (t, 2H); 3.20–3.70 (m, 4H); 3.80 (s, 2H); 4.25 (s, 4H); 5.85 (s, 1H); 6.75 (t, 1H); 6.80 (d, 2H); 7.05 (d, 1H); 7.30 (s, 1H); 7.40 (s, 1H); 7.60 (d, 1H); 11.10 (s, 1H). MS m/z (%): 395 (MH+, 1%), 178 (100%).

6-Chloro-3-[2-[4-(2,3-dihydrobenzofuran-7-yl)-1,2,3,6-tetrahydropyridin-1-yl]ethyl]-1H-indole oxalate, 1x, mp 211–14° C. $^1$H NMR (DMSO-$d_6$): 2.75 (s, 2H); 3.05–3.15 (m, 2H); 3.20 (t, 2H), 3.25–3.50 (m, 4H); 3.85 (s, 2H), 4.55 (t, 2H); 6.30 (s, 1H); 6.85 (t, 1H); 7.00 (d, 1H); 7.10 (d, 1H); 7.15 (d, 1H); 7.30 (s, 1H); 7.40 (s, 1H); 7.60 (d, 1H); 11.10 (s, 1H). MS m/z (%): 379 (MH+, 3%),178 (100%).

3-[2-[4-(Benzofuran-7-yl)-1,2,3,6-tetrahydropyridin-1-yl]ethyl]-6-chloro-1H-indole hemifumarate, 1y, mp 214–20° C. $^1$H NMR (DMSO-$d_6$): 2.65 (s, 2H); 2.75–2.85 (m, 4H); 2.90–3.00 (m, 2H); 3.10–3.50 (m, 3H); 6.55 (s, 2H); 6.90–7.00 (m, 2H); 7.15–7.30 (m, 3H); 7.35 (s, 1H); 7.50–7.60 (m, 2H); 8.00 (s, 1H); 10.90 (s, 1H). MS m/z (%): 377 (MH+, 25%),178 (73%), 143(22%).

3-[2-[4-(Benzofuran-7-yl)-1,2,3,6-tetrahydropyridin-1-yl]ethyl]-5-bromo-1H-indole oxalate, 1z, mp 185–94° C. $^1$H NMR (DMSO-$d_6$): 2.90 (s, 2H); 3.10–3.20 (m, 2H); 3.25–3.55 (m, 4H); 3.95 (s, 2H); 6.60 (s, 2H); 7.00 (m, 1H); 7.20 (s, 1H); 7.20–7.45 (m, 4H); 7.60 (d, 1H); 7.80 (s, 1H); 8.05 (s, 1H); 11.20 (s, 1H). MS m/z (%): 423 (MH+($^{81}$Br), 22%), 421 (MH+($^{79}$Br), 20%), 224 (70%), 222(72%),143 (33%).

3-[2-[4-(Benzofuran-7-yl)-1,2,3,6-tetrahydropyridin-1-yl]ethyl]-5-fluoro-1H-indole hemioxalate, 1aa, mp 176–79° C. $^1$H NMR (DMSO-$d_6$): 2.75 (s, 2H); 2.90–3.25 (m, 6H); 3.65 (s, 2H); 6.60 (s, 1H); 6.85–6.95 (m, 1H); 7.00 (s, 1H); 7.20–7.40 (m, 5H); 7.60 (d, 1H); 8.00 (s, 1H); 11.00 (s, 1H). MS m/z (%): 361 (MH+, 12%), 162(100%),115(13%).

3-[2-[4-(Benzofuran-7-yl)piperidin-1-yl]ethyl]-6-chloro-1H-indole hemifumarate, 1bb, mp 245–50° C. $^1$H NMR (DMSO-$d_6$):1.85–2.00 (m, 4H); 2.75 (t, 2H); 2.90 (t, 2H); 3.05 (tt, 1H); 3.25 (d, 2H); 6.55 (s, 2H); 6.95 (s, 1H); 7.00 (d, 1H); 7.15–7.25 (m, 3H); 7.40 (s, 1H); 7.50 (d, 1H); 7.55 (d, 1H); 8.00 (s, 1H); 10.95 (s, 1H). MS m/z (%): 379 (MH+, 5%), 214 (10%), 178(20%), 143(100%).

3-[2-[4-(Benzofuran-7-yl)piperidin-1-yl]ethyl]-5-fluoro-1H-indole oxalate, 1 cc, mp 191–94° C. $^1$H NMR (DMSO-$d_6$): 2.05–2.25 (m, 4H); 3.05–3.20 (m, 4H); 3.20–4.40 (m, 3H), 3.60–3.70 (m, 2H); 6.90–7.00 (m, 2H), 7.15–7.25 (m, 2H); 7.35–7.45 (m, 3H); 7.55 (d, 1H), 8.00 (s, 1H); 11.05 (s, 1H). MS m/z (%). 363 (MH+, 5%), 214 (9%), 161 (10%), 143 (24%).

3-[2-[4-(Benzofuran-7-yl)piperidin-1-yl]ethyl]-5-bromo-1H-indole oxalate, 1dd, mp 153–57° C. $^1$H NMR (DMSO-$d_6$): 2.05–2.20 (m, 4H); 3.05–3.20 (m, 4H); 3.20–3.40 (m, 3H); 3.70 (d, 2H); 6.95 (s, 1H); 7.15–7.25 (m, 3H); 7.30–7.40 (m, 2H); 7.55 (d, 1H); 7.80 (s, 1H); 8.00 (s, 1H); 11.20 (s, 1H). MS m/z (%): 423 (MH+, 36%), 224 (27%), 202 (45%), 143 (27%), 117 (18%).

Example 2

3-[2-[4-(1,4-Benzodioxan-5-yl)Piperazin-1-yl] Ethyl]-1H-Indole Hemifumarate, 2a

A mixture of 3-(2-bromoethyl)-1H-indole (1.5 g), 1-(1,4-benzodioxan-5-yl)piperazine (1.2 g), potassium carbonate (1.9 g), and potassium iodide (0.1 g) in methylisobutyl ketone (100 mL) was refluxed for 16 h. Standard workup with ethyl acetate gave an oil which was purified by flash chromatography (eluent: heptane/ethanol/ethyl acetate/triethylamine 15:2:2:1). The fumarate salt was obtained from an ethanol solution by addition of fumaric acid. Recrystallization from ethanol gave the hemifumarate 2a (0.9 g). Mp: 204–7° C. $^1$H NMR (DMSO-$d_6$): 2.60–2.80 (m, 6H); 2.90 (t, 2H); 2.95–3.10 (m, 4H); 4.15–4.30 (m, 4H); 6.50 (d, 1H); 6.55 (d, 1H); 6.60 (s, 1H); 6.75 (t, 1H); 7.00 (t, 1H); 7.10 (t, 1H); 7.20 (s, 1H); 7.35 (d, 1H); 7.55 (d, 1H); 10.75 (s, 1H). MS m/z (%): 364 (MH+, 5%), 233 (57%), 218 (21%), 190 (19%), 144 (54%), 70 (100%).

1-Acetyl-3-[2-[4-(1,4-benzodioxan-4-yl)piperazin-1-yl]ethyl]-2,3-dihydro-1H-indole, 2b, mp 119–20° C. $^1$H NMR (DMSO-$d_6$) 1.90 (d, 1H); 2.20 (s, 4H); 2.95–3.30 (m, 11H); 3.40–3.50 (m, 1H); 3.75–3.85 (m, 1H); 4.20–4.30 (m, 4H); 6.45 (dd, 1H); 6.55 (dd, 1H); 6.75 (t, 1H);7.00 (t, 1H);7.20 (t, 1H); 7.30 (d, 1H); 8.05 (d, 1H). MS m/z (%): 408 (MH+, 54%), 233 (17%), 178 (100%), 119 (20%).

Example 3

3-[2-[4-(1,4-Benzodioxan-5-yl)Piperazin-1-yl] Ethyl]-6-Chloro-1H-Indole Hemifumarate, 3a A mixture of 2-(6-chloro-1H-indol-3-yl)acetic acid (2.0 g), 1-(1,4-benzodioxan-5-yl)piperazine (3.6 g), N,N-dicyclohexylcarbodiimide (2.4 g), and 4-dimethylaminopyridine (0.2 g) in dry tetrahydrofuran (100 mL) was stirred for 16 h at room temperature under a nitrogen atmosphere. Filtration and standard workup with methylene chloride gave an oil which was purified by flash chromatography (eluent: ethyl acetate/heptane/methanol 16:3:1 giving 3-[2-[4-(1,4-benzodioxan-5-yl)piperazin-1-yl]-2-oxoethyl]-6-chloro-1H-indole as an oil (2.0 g).

The oil was dissolved in tetrahydrofuran (25 mL) and added dropwise to a suspension of lithium aluminium hydride (0.9 g) in dry tetrahydrofuran (50 mL) at room temperature followed by reflux for 3 h. Quench with 2 M aq. sodium hydroxide and standard workup gave the free base of 3a as an oil (1.9 g). The hemifumarate salt, 3a (1.0 g), was obtained from an ethanol solution by addition af fumaric acid. Mp: 215–16° C. $^1$H NMR (DMSO-$d_6$): 2.60–2.85 (m, 6H); 2.85–2.95 (m, 2H); 2.95–3.10 (m, 4H); 4.10–4.30 (m, 4H); 6.45 (d, 1H); 6.50 (d, 1H); 6.60 (s, 1H); 6.70 (t, 1H); 7.0 (dd, 1H); 7.25 (d, 1H); 7.40 (d, 1H); 7.55 (d, 1H); 10.95 (s, 1H). MS m/z (%): 398 (MH+, 10%), 234 (13%), 233 (100%), 178 (12%).

The following compounds were prepared analogously:

3-[2-[4-(5-Chloro-2, 2-dimethyl-2,3-dihydrobenzofuran-7-yl)piperazin-1-yl]ethyl]-1H-indole hemifumarate, 3b, mp 210–12° C. $^1$H NMR (DMSO-$d_6$): 1.40 (s, 6H); 2.55–2.75 (m, 6H); 2.80–3.00 (m, 4H); 3.05–3.20 (m, 4H); 6.60 (s, 1H); 6.65 (d, 1H); 6.80 (d, 1H); 6.95 (t, 1H); 7.05 (t, 1H); 7.15 (d, 1H); 7.35 (d, 1H); 7.55 (d, 1H); 10.70 (s, 1H). MS m/z (%): 410 (MH+, 18%), 281 (32%), 279 (100%), 144 (39%).

6-Chloro-3-[2-[4-(5-chloro-3,3-dimethyl-2,3-dihydrobenzofuran-7-yl)piperazin-1-yl]ethyl]-1H-indole hemifumarate, 3c, mp 130–32° C. $^1$H NMR (DMSO-$d_6$): 1.25 (s, 6H); 2.55–2.70 (m, 6H); 2.85 (t, 2H); 3.00–3.20 (m, 4H); 4.25 (s, 2H); 6.60 (s, 1H); 6.65 (s, 1H); 6.85 (s, 1H); 7.00 (d, 1H); 7.20 (s, 1H); 7.35 (s, 1H); 7.55 (d, 1H); 10.90 (s, 1H). MS m/z (%): 446 (8%), 444 (MH+, 11%), 281 (34%), 280 (16%), 279 (100%), 178 (15%).

6-Chloro-3-[2-[4-(6-chloro-2,2-dimethyl-3,4-dihydro-2H-1-benzopyran-8-yl)piperazin-1yl]ethyl]-1H-indole fumarate, 3d, mp 224–25° C. ($^1$H NMR (DMSO-$d_6$). 1.30 (s, 6H); 1.70 (t, 2H); 2.60–2.75 (m, 8H); 2.90 (t, 2H); 2.95–3.10 (m, 4H); 6.60 (s, 1H); 6.65 (d, 1H); 6.70 (d, 1H); 7.00 (d, 1H); 7.20 (s, 1H); 7.35 (s, 1H); 7.55 (d, 1H); 10.95 (s, 1H). MS m/z (%) 458 (MH+, 11%), 295 (32%), 293 (100%), 259 (11%), 178 (14%)

6-Chloro-3-[2-[4-(2, 2-dimethyl-2,3-dihydrobenzofuran-7-yl)piperazin-1-yl]ethyl]-1H-indole fumarate, 3e, mp 165–67° C. $^1$H NMR (DMSO-$d_6$): 1.40 (s, 6H); 2.65–280 (m, 6H); 290 (t, 2H); 2.95 (s, 2H); 3.00–3.20 (m, 4H); 6.60 (s, 1H); 6.65 (d, 1H); 6.70 (t, 1H); 6.75 (d, 1H); 7.00 (d, 1H); 7.20 (s, 1H); 7.35 (s, 1H); 7.55 (d, 1H). MS m/z (%): 410 (MH+, 6%), 245 (67%), 209 (39%), 178 (8%), 127 (51%), 45 (100%).

1-[2-[4-(1,4-Benzodioxan-5-yl)piperazin-1-yl]ethyl]-6-chloro-1H-indole oxalate, 3f, mp 234–35° C. $^1$H NMR (DMSO-$d_6$): 2.85 (s, 4H); 2.95–3.15 (m, 6H); 4.15–4.30 (m, 4H); 4.40 (t, 2H); 6.45–6.55 (m, 3H); 6.70 (t, 1H); 7.05 (t, 1H); 7.45 (d, 1H); 7.55 (d, 1H); 7.70 (s, 1H). MS m/z (%): 398 (MH+, 45%), 218 (100%),178 (50%).

1-[2-[4-(1,4-Benzodioxan-5-yl)piperazin-1-yl]ethyl]-5-chloro-1H-indole oxalate, 3g, mp 234–35° C. $^1$H NMR (DMSO-$d_6$): 2.85 (s, 4H); 2.95–3.15 (m, 6H); 4.15–4.30 (m, 4H); 4.45 (t, 2H); 6.40–6.50 (m, 2H); 6.55 (d, 1H); 6.70 (t, 1H); 7.15 (d, 1H); 7.50 (s, 1H); 7.55–7.65 (m, 2H). MS m/z (%): 398 (MH+; 44%), 218 (100%), 178 (62%).

1-[2-[4-(1,4-Benzodioxan-5-yl)piperazin-1-yl]ethyl]-5-fluoro-1H-indole oxalate, 3h, mp 230–31° C. $^1$H NMR (DMSO-$d_6$): 2.90 (s, 4H); 2.95–3.20 (m, 6H); 4.15–4.30 (m, 4H); 4.45 (t, 2H); 6.40–6.50 (m, 2H); 6.55 (d, 1H); 6.75 (t, 1H); 7.00 (t, 2H); 7.30 (d, 1H); 7.50 (s, 1H); 7.50–7.55 (m, 1H). MS m/z (%): 382 (MH+, ?), 218 (63%),162 (100%).

1-[2-[4-(1,4-Benzodioxan-5-yl)piperazin-1-yl]ethyl]-1H-indole oxalate, 3i, mp 225–29° C. $^1$H NMR (DMSO-$d_6$): 2.95 (s, 4H); 3.05–3.20 (m, 6H); 4.10–4.30 (m, 4H); 4.45 (t, 2H); 6.40–6.50 (m, 2H); 6.55 (d, 1H); 6.75 (t, 1H); 7.05 (t, 1H); 7.40 (s, 1H); 7.55 (t, 2H). MS m/z (%): 364 (MH+, 100%), 218 (85%), 146 (80%).

1-[2-[4-(2,3-Dihydrobenzofuran-7-yl)piperazin-1-yl]ethyl]-1H-indole oxalate, 3j, mp 223–26° C. $^1$H NMR (DMSO-$d_6$): 2.85 (s, 4H); 3.00 (t, 2H); 3.05–3.20 (m, 6H); 4.40 (t, 2H); 4.50 (t, 2H); 6.45 (d, 1H); 6.65 (d, 1H); 6.75 (t, 1H); 6.85 (d, 1H); 7.00 (t, 1H); 7.15 (t, 1H); 7.40 (d, 1H); 7.55 (dd, 2H). MS m/z (%): 348 (MH+, 38%), 231 (50%), 201 (100%), 174 (25%), 162 (41%), 146 (98%).

Example 4

3-[2-[4-(1,4-Benzodioxan-5-yl)Piperazin-1-yl] Ethyl]-2,3-Dihydro-1H-Indole Sesquioxalate, 4a A solution of 2a (16 g) in trifluoroacetic acid (200 mL) was treated in portions with sodium borohydride (2×2.9 g, 1.5 hour interval) at room temperature followed by stirring for 2.5 hours at room temperature. The reaction mixture was poured onto ice and made alkaline with aq. sodium hydroxide followed by standard work-up. The resulting oil was purified by flash chromatography (eluent: heptane/ethyl acetate/ethanol/triethylamine 15:2:2:1) giving the title base as a yellow oil (13.8 g). The title oxalate was as obtained from the free base (1.4 g) as crystalline material from ethanol by addition of oxalic acid (0.9 g). Mp 145–50° C. $^1$H NMR (DMSO-$d_6$): 1.75–1.85 (m, 1H); 2.05–2.15 (m, 1H); 2.95–3.30 (m, 12H); 3.60 (t, 1H); 4.20 (d, 4H); 6.50 (d, 2H); 6.60 (d, 2H); 6.75 (t, 1H); 6.95 (t, 1H); 7.10 (d, 1H). MS m/z (%): 366 (MH+, 10%), 221 (10%), 178 (14%), 150 (20%), 118 (100%).

The following compounds were prepared analogously:

3-[2-[4-(1,4-Benzodioxan-5-yl)piperazin-1-yl]ethyl]-2,3-dihydro-5-fluoro-1H-indole hemioxalate, 4b, mp 201–5° C. $^1$H NMR (DMSO-$d_6$): 1.60–1.80 (m, 1H); 1.95–2.10 (m, 1H); 2.60–3.30 (m, 12H); 3.35 (t, 1H); 4.20 (d, 4H); 6.35–6.55 (m, 3H); 6.15–6.25 (m, 2H); 6.90 (d, 1H). MS m/z (%): 384 (MH+, 32%), 178 (28%), 150 (12%), 136 (100%).

3-[2-[4-(1,4-Benzodioxan-5-yl)piperazin-1-yl]ethyl]-5-chloro-2,3-dihydro-1H-indole oxalate, 4c, mp 153–57° C. $^1$H NMR (DMSO-$d_6$): 1.70–1.85 (m, 1H); 2.05–2.20 (m, 1H); 2.85–3.05 (m, 2H); 3.05–3.35 (m, 10H); 3.60 (t, 2H); 4.15–4.30 (m, 4H); 6.45–6.60 (m, 3H); 6.75 (t, 1H); 6.95 (dd, 1H); 7.10 (d, 1H). MS m/z (%): 400 (MH+, 39%), 178 (39%), 152 (100%).

3-[2-[4-(1,4-Benzodioxan-5-yl)piperazin-1-yl]ethyl]-6-chloro-2,3-dihydro-1H-indole oxalate, 4d, mp 185–88° C. $^1$H NMR (DMSO-$d_6$): 1.75–1.85 (m, 1H); 2.00–2.10 (m, 1H); 2.90–3.30 (m, 12H); 3.60 (t, 1H); 4.15–4.30 (m, 4H); 6.45 (s, 1H); 6.50 (d, 1H); 6.55 (t, 2H); 6.75 (t, 1H); 7.05 (d, 1H) MS m/z (%): 400 (MH+, 14%), 221 (52%), 180 (22%), 152 (100%)

Example 5

3-[2-[4-(1,4-Benzodioxan-5-yl)Piperazin-1-yl] Ethyl]-1-Butyl-1H-Indole Oxalate, 5a A solution of 2a (1.0 g) in dry tetrahydrofuran (50 mL) was added dropwise to a suspension of sodium hydride (60% in mineral oil, 0.14 g) in tetrahydrofuran (25 mL) at room temperature. After stirring for 30 min a solution of 1-bromobutane (0.85 g) in dry tetrahydrofuran (10 mL) was added dropwise. Stirring for 1 hour followed by standard work-up with ethyl acetate gave an oil which was purified by flash chromatography (eluent: heptane/ethyl acetate/triethylamine 15:3:2). The resulting oil was converted to the title oxalate salt (0.7 g) from acetone by addition of oxalic acid. Mp 168–74° C. $^1$H NMR (DMSO-$d_6$): 0.90 (t, 3H); 1.25 (qv, 2H); 1.70 (qv, 2H); 3.05 (t, 2H); 3.15–3.40 (m, 8H); 4.10 (t, 2H); 4.15–4.30 (m, 4H); 6.55 (d, 1H); 6.60 (d, 1H); 6.75 (t, 1H); 7.05 (t, 1H); 7.15 (t, 1H); 7.25 (s, 1H); 7.45 (d, 1H); 7.60 (d, 1H). MS m/z (%): 420 (MH+, 33%), 233 (39%), 200 (100%), 158 (36%).

The following compounds were prepared analogously:

1-Allyl-3-[2-[4-(1,4-benzodioxan-5-yl)piperazin-1-yl] ethyl]-1H-indole oxalate, 5b, mp 187–90° C. $^1$H NMR (DMSO-$d_6$): 3.05 (t, 2H); 3.10–3.40 (m, 10H); 4.20 (d, 4H); 4.75 (d, 2H); 5.05 (d, 1H); 5.15 (d, 1H); 5.90–6.05 (m, 1H); 6.50 (d, 1H); 6.55 (d, 1H); 6.75 (t, 1H); 7.05 (t, 1H); 7.15 (t, 1H); 7.25 (s, 1H); 7.40 (d, 1H); 7.60 (d, 1H). MS m/z (%): 404 (MH+, 38%), 233 (38%), 184 (43%), 120 (29%).

3-[2-[4-(1,4-Benzodioxan-5-yl)piperazin-1-yl]ethyl]-1-propargyl-1H-indole oxalate, 5c, mp 168–72° C. $^1$H NMR (DMSO-$d_6$): 3.00–3.30 (m, 12H); 3.40 (t, 1H); 4.25 (d, 4H); 5.05 (d, 2H); 6.50 (d, 2H); 6.55 (d, 1H); 7.10 (t, 1H); 7.20 (t, 1H); 7.30 (s, 1H); 7.50 (d, 1H); 7.65 (d, 1H). MS m/z (%): 402 (MH+, 52%), 233 (50%),182 (57%),167 (100%).

Example 6

3-[2-[4-(1,4-Benzodioxan-5-yl)Piperazin-1-yl] Ethyl]-2,3-Dihydro-1-Methyl-1H-Indole Oxalate, 6a A solution of 4a (1.5 g) in dry tetrahydrofuran (50 mL) was added dropwise to a suspension of sodium hydride (60% in mineral oil, 0.21 g) in tetrahydrofuran (25 mL) at room temperature. After stirring for 30 min a solution of iodomethane (0.75 g) in dry tetrahydrofuran (25 mL) was added dropwise. Stirring for 1 hour followed by standard work-up with ethyl acetate gave an oil which was purified by flash chromatography (eluent: heptane/ethyl acetate/triethylamine 15:3:2). The resulting oil was converted to the title oxalate salt (0.3 g) from acetone by addition of oxalic acid. Mp 155–65° C. $^1$H NMR (DMSO-$d_6$) 1.75–1.85 (m, 1H); 2.05–2.15 (m, 1H); 2.70 (s, 3H); 2.90–3.25 (m, 12H); 3.40 (t, 1H); 4.15–4.30 (m, 4H); 6.45–6.55 (m, 3H); 6.65 (t, 1H); 6.75 (t, 1H); 7.05 (t, 1H); 7.10 (d, 1H). MS m/z (%): 380 (MH+, 4%), 178 (4%), 132 (53%).

The following compounds were prepared analogously:

3-[2-[4-(1,4-Benzodioxan-5-yl)piperazin-1-yl]ethyl]-1-benzyl-2,3-dihydro-1H-indole oxalate, 6b, mp 158–65° C. $^1$H NMR (DMSO-$d_6$): 1.75–1.85 (m, 1H); 2.10–2.20 (m, 1H); 2.90–3.30 (m, 12H); 3.45 (t, 1H); 4.15–4.25 (m, 5H); 4.35 (d, 1H); 6.50 (d, 1H); 6.55 (d, 1H); 6.65–6.70 (m, 2H); 6.75 (t, 1H); 7.00 (t, 1H); 7.10 (d, 1H); 7.30 (t, 1H); 7.35 (s, 4H). MS m/z (%): 456 (MH+, 19%), 236 (25%), 178 (100%), 130 (11%).

1-Allyl-3-[2-[4-(1,4-benzodioxan-5-yl)piperazin-1-yl] ethyl]-2,3-dihydro-1H-indole oxalate, 6c, mp 133–36° C. $^1$H NMR (DMSO-$d_6$): 1.75–1.85 (m, 1H); 2.10–2.20 (m, 1H); 2.95–3.35 (m, 12H); 3.50 (t, 1H); 3.65 (dd, 1H); 3.75 (dd, 1H); 4.25 (d, 4H); 5.15 (d, 1H); 5.30 (d, 1H); 5.85–5.95 (m, 1H); 6.50 (d, 1H); 6.55 (d, 2H); 6.65 (t, 1H); 6.75 (t, 1H); 7.00 (t, 1H); 7.10 (d, 1H). MS m/z (%): 406 (MH+, 15%), 178 (178%), 158 (24%), 130 (31%), 117 (20%).

Example 7

1-Acetyl-3-[2-[4-(1,4-benzodioxan-5-yl)piperazin-1-yl]ethyl]-1H-indole oxalate, 7a A mixture of 2a (2.0 g), tetrabutylammonium hydrogen sulfate (0.2 g), sodium hydroxide (1.0 g), and methylene chloride (40 mL) was stirred for 10 min followed by dropwise addition of a solution of acetyl chloride (0.97 g) in methylene chloride at room temperature. After stirring for 1 hour water was added followed by standard work-up. The resulting oil was purified by flash chromatography (eluent heptane/ethyl acetate/ethanol/triethylamine 17:1:1) giving a yellow oil which was converted to the title oxalate salt (0.75 g) from acetone by addition of oxalic acid. Mp 199–202° C. $^1$H NMR (DMSO-$d_6$): 2.65 (s, 3H); 3.05 (t, 2H); 3.15 (s, 10H); 4.20 (d, 2H); 4.25 (d, 2H); 6.50 (d, 1H); 6.55 (d, 1H); 6.75 (t, 1H); 7.30–7.40 (m, 2H); 7.70 (d, 1H); 7.80 (s, 1H); 8.35 (d, 1H) MS m/z (%):406 (MH+, 28%), 233 (44%), 218 (39%),144 (100%).

Pharmacological Testing

The affinity of the compounds of the invention to 5-HT$_{1A}$ receptors was determined by measuring the inhibition of binding of a radioactive ligand at 5-HT$_{1A}$ receptors as described in the following test:

Inhibition of $^3$H-5-CT Binding to Human 5-HT$_{1A}$ Receptors

By this method the inhibition by drugs of the binding of the 5-HT$_{1A}$ agonist $^3$H-5-carboxamido tryptamine ($^3$H-5-CT) to cloned human 5-HT$_{1A}$ receptors stably expressed in transfected HeLa cells (HA7) (Fargin, A. et al, *J. Biol. Chem.*, 1989, 264, 14848) is determined in vitro. The assay was performed as a modification of the method described by Harrington, M. A. et al, *J. Pharmacol. Exp. Ther.*, 1994, 268, 1098. Human 5-HT$_{1A}$ receptors (40 μg of cell homogenate) were incubated for 15 minutes at 37° C. in 50 mM Tris buffer at pH 7.7 in the presence of $^3$H-5-CT. Non-specific binding was determined by including 10 μM of metergoline. The reaction was terminated by rapid filtration through Unifilter GF/B filters on a Tomtec Cell Harvester. Filters were counted in a Packard Top Counter. The results obtained are presented in table 1:

TABLE 1

| Compound No. | Inhibition of $^3$H-5-CT binding IC$_{50}$ (nM) |
|---|---|
| 1a | 17 |
| 1b | 7.2 |
| 1c | 2.5 |
| 1d | 55 |
| 1e | 11 |
| 1f | 6.1 |
| 1g | 2.8 |
| 1h | 4.6 |
| 1i | 6.9 |
| 1j | 14 |
| 1k | 2.0 |
| 1l | 12 |
| 1m | 99 |
| 1n | 8.2 |
| 2a | 2.9 |
| 2b | 13 |
| 1v | 0.81 |
| 3a | 1.2 |
| 3b | 3.6 |
| 3d | 21 |
| 4d | 14 |
| Pindolol* | 100 |

*reference compound

The compounds of the invention have also been tested for their effect on re-uptake of serotonin in the following test:

Inhibition of $^3$H-5-HT Uptake Into Rat Brain Synaptosomes

Using this method the ability of drugs to inhibit the accumulation of $^3$H-5-HT into whole rat brain synaptosomes is determined in vitro. The assay was performed as described by Hyttel, J., Psychopharmacology 1978, 60, 13 The results obtained are presented in table 2:

TABLE 2

| Compound No | Inhibition of serotonin reuptake IC$_{50}$ (nM) |
|---|---|
| 1a | 5.0 |
| 1b | 2.8 |
| 1c | 45 |
| 1d | 36 |
| 1e | 0.25 |
| 1f | 5.9 |
| 1g | 3.8 |
| 1h | 1.7 |
| 1i | 6.8 |
| 1j | 3.5 |
| 1k | 18 |
| 1l | 7.7 |
| 1m | 57 |
| 1n | 2.1 |
| 1v | 0.85 |
| 2a | 3.5 |
| 2b | 12 |
| 3a | 5.3 |
| 3b | 8.3 |
| 3d | 15 |
| 4d | 4.3 |
| Paroxetine* | 0.29 |

*reference compound

The 5-HT$_{1A}$ antagonistic activity of some of the compounds of the invention has been estimated in vitro at cloned 5-HT$_{1A}$ receptors stably expressed in transfected HeLa cells (HA7). In this test 5-HT$_{1A}$ antagonistic activity is estimated by measuring the ability of the compounds to antagonize the 5-HT induced inhibition of forskolin induced cAMP accumulation. The assay was performed as a modification of the method described by Pauwels, P. J et al, Biochem. Pharmacol. 1993, 45, 375. The results obtained are presented in table 3:

TABLE 3

| Compound No. | Antagonism of Inhibition of forskolin induced cAMP accumulation IC$_{50}$ (nM) |
|---|---|
| 1a | 2900 |
| 1b | 5000 |
| 1e | 2400 |
| 1f | 1800 |
| 1g | 1800 |
| 1h | 280 |
| 1i | 620 |
| 1j | 980 |
| 1k | 580 |
| 1n | 1900 |
| 1o | 3200 |
| 1t | 5900 |
| 1u | 2000 |
| 1v | 3300 |
| 1x | 3000 |
| 2a | 160 |
| 2b | 250 |
| 3a | 500 |
| 3c | 2600 |
| 3d | 2300 |
| 4d | 890 |
| 6a | 100 |
| Pindolol* | 270 |

*reference compound

Some of the compounds of the invention have also been tested for their in vivo effect on 5-HT$_{1A}$ receptors in the assay described by Sánchez. C. Et al., Eur. J Pharmacol, 1996, 315, pp 245. In this test antagonistic effects of test compounds are determined by measuring the ability of the test compounds to inhibit 5-MeO-DMT induced 5-HT syndrome.

The compounds of the present invention possess valuable activity as serotonin re-uptake inhibitors and have antagonistic effect at 5-HT$_{1A}$ receptors. The compounds of the invention are therefore considered useful for the treatment of diseases and disorders responsive to the inhibition of serotonin re-uptake and antagonistic activity at 5-HT$_{1A}$ receptors. Diseases responsive to the inhibition of serotonin re-uptake are well known in the art and include affective disorders, such as depression, psychosis, anxiety disorders including general anxiety disorder, panic disorder, obsessive compulsive disorder, etc.

As explained above, the antagonistic activity at 5-HT$_{1A}$ receptors of the compounds of the invention will counteract the negative feed back mechanism induced by the inhibition of serotonin reuptake and is thereby expected to improve the effect of the serotonin reuptake inhibiting activity of the compounds of the invention.

The compounds as claimed herein are therefore considered to be particularly useful as fast onset of action medicaments for the treatment of depression. The compounds may also be useful for the treatment of depressions which are non-responsive to currently available SSRI's.

Pharmaceutical Formulation

The pharmaceutical formulations of the invention may be prepared by conventional methods in the art. For example: Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilization of the solution and filling in suitable ampules or vials Any suitable additive conventionally used in the art may be added, such as tonicity agents, preservatives, antioxidants, etc.

The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients, or other additives normally used in the art may be used.

Conveniently, the compounds of the invention are administered in unit dosage form containing said compounds in an amount of about 0.01 to 1000 mg The total daily dose is usually in the range of about 0.05–500 mg, and most preferably about 0.1 to 50 mg of the active compound of the invention.

What is claimed is:

1. An indole or 2,3-dihydro-indole derivative of the formula:

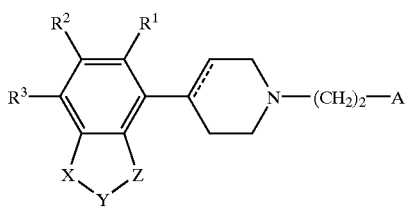

any of its enantiomers or any mixture thereof, or an acid addition salt thereof, wherein X is —O— or —S—, or —CR$^4$R$^5$—; and
Y is —CR$^6$R$^7$—, —CR$^6$R$^7$—CR$^8$R$^9$—, or —CR$^6$=CR$^7$—; or
X and Y together form a group —CR$^4$=CR$^5$—, or —CR$^4$=CR$^5$—CR$^6$R$^7$—;
Z is —O— or —S—;
A is selected from a group of formula (II) and (IV)

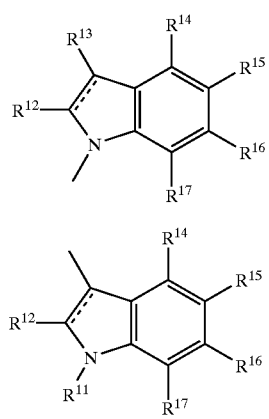

wherein the dotted lines mean an optional bond;
R$^1$, R$^2$, R$^3$, R$^{12}$, R$^{13}$, R$^{14}$, R$^{15}$, R$^{16}$ and R$^{17}$ are each independently selected from hydrogen, halogen, trifluoromethyl, alkyl, alkenyl, alkynyl, cycloalkyl, alkoxy, hydroxy, formyl, acyl, amino, alkylamino, dialkylamino, acylamino, alkoxycarbonylamino, aminocarbonylamino, alkylaminocarbonylamino, dialkylaminocarbonylamino, nitro and cyano;
R$^4$, R$^5$, R$^6$, R$^7$, R$^8$ and R$^9$ are each independently selected from hydrogen and alkyl; and
R$^{11}$ is selected from hydrogen, alkyl, alkenyl, alkynyl, cycloalkyl, phenyl, naphthyl, phenylalkyl, acyl and formyl.

2. The compounds of claim 1 wherein Z is —O—.
3. The compounds of claim 1 wherein Z is —S—.
4. The compounds of claim 1 wherein A is a group of formula (II).
5. The compounds of claim 1 wherein A is a group of formula (IV).
6. The compounds of claim 2 wherein A is a group of formula (II).
7. The compounds of claim 2 wherein A is a group of formula (IV).
8. The compounds of claim 3 wherein A is a group of formula (II).
9. The compounds of claim 3 wherein A is a group of formula (IV).
10. The compounds of claim 1 wherein R$^4$, R$^5$, R$^6$, R$^7$, R$^8$ and R$^9$ are selected from hydrogen or methyl.

11. The compounds of claim 1 selected from the group consisting of
6-Chloro-3-[2-[4-(2,2,5-trimethyl-2,3-dihydrobenzofuran-7-yl)piperidin-1-yl]ethyl]-1H-indole;
6-Chloro-3-[2-[4-(2,2,-dimethyl-2,3-dihydrobenzofuran-7-yl)piperidin-1-yl]ethyl]-1H-indole;
6-Chloro-3-[2-[4-(2,2,-dimethyl-2,3-dihydrobenzofuran-7-yl)-1,2,3,6-tetrahydro-1-pyridy]ethyl]-1H-indole;
3-[2-[4-(1,4-Benzodioxan-5-yl)-1,2,3,6-tetrahydropyridin-1-yl]ethyl]-5-chloro-1H-indole;
3-[2-[4-(1,4-Benzodioxan-5-yl)-1,2,3,6-tetrahydropyridin-1-yl]ethyl]-5-fluoro-1H-indole;
3-[2-[4-(1,4-Benzodioxan-5-yl)piperidin-1-yl]ethyl]-6-chloro-1H-indole;
3-[2-[4-(1,4-Benzodioxan-5-yl)piperidin-1-yl]ethyl]-5-chloro-1H-indole;
3-[2-[4-(1,4-Benzodioxan-5-yl)piperidin-1-yl]ethyl]-5-fluoro-1H-indole;
6-Chloro-3-[2-[4-(2,3-dihydrobenzofuran-7-yl)-1,2,3,6-tetrahydropyridin-1-yl]ethyl]-1H-indole;
3-[2-[4-(Benzofuran-7-yl-1,2,3,6-tetrahydropyridin-1-yl]ethyl]-6-chloro-1H-indole;
3-[2-[4-(Benzofuran-7-yl-1,2,3,6-tetrahydropyridin-1-yl]ethyl]-5-bromo-1H-indole;
3-[2-[4-(Benzofuran-7-yl-1,2,3,6-tetrahydropyridin-1-yl]ethyl]-5-fluoro-1H-indole;
3-[2-[4-(Benzofuran-7-yl)piperidin-1-yl]ethyl]-6-chloro-1H-indole;
3-[2-[4-(Benzofuran-7-yl)piperidin-1-yl]ethyl]-5-fluoro-1H-indole;
3-[2-[4-(1,4-Benzodioxan-5-yl)-1,2,3,6-tetrahydro-1-pyridyl]ethyl]-6-chloro-1H-indole:
3-[2-[4-(1,4-Benzodioxan-5-yl)-piperidin-1-yl]ethyl]-6-chloro-1H-indole; and
3-[2-[4-(Benzofuran-7-yl)piperidin-1-yl]ethyl]-5-bromo-1H-indole;
or an acid addition salt thereof.

12. A method of treating a disorder or disease of a living animal body, said disorder or disease selected from the group consisting of an affective disorder, anxiety disorder, panic disorder and obsessive compulsive disorder, comprising administering to said living animal body a therapeutically effective amount of a compound of claim 1, or a pharmaceutically acceptable acid addition salt thereof.

13. An indole or 2,3-dihydro-indole derivative of the formula:

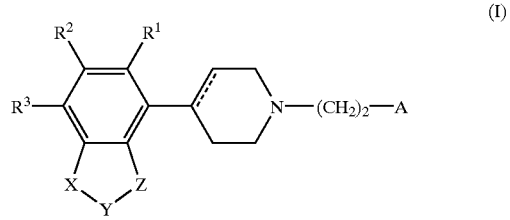

any of its enantiomers or any mixture thereof, or an acid addition salt thereof, wherein X is —O— or —S—, or —CR$^4$R$^5$—; and
Y is —CR$^6$R$^7$—CR$^8$R$^9$—, or —CR$^6$=CR$^7$—; or X and Y together toxin a group —CR⁴=CR⁵—, or —R⁴=CR⁵—CR⁶R⁷—;

Z is —O— or —S—;

provided that when X and Z are both O, then Y is —CR⁶R⁷—CR⁸R⁹— or CR⁶=CR⁷—;

A is selected from a group of formula (II), (III) and (IV)

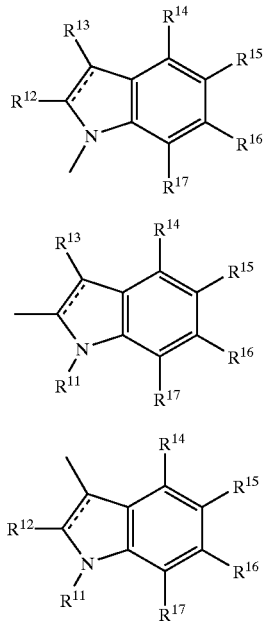

wherein the dotted lines mean an optional bond;

$R^1$, $R^2$, $R^3$, $R^{12}$, $R^{13}$, $R^{14}$, $R^{15}$, $R^{16}$ and $R^{17}$ are each independently selected from hydrogen, halogen, trifluoromethyl, alkyl, alkenyl, alkynyl, cycloalkyl, alkoxy, hydroxy, formyl, acyl, amino, alkylamino, dialkylamino, acylamino, alkoxycarbonylamino, aminocarbonylamino, alkylaminocarbonylamino, dialkylaminocarbonylamino, nitro and cyano;

$R^4$, $R^5$, $R^6$, $R^7$, $R^8$ and $R^9$ are each independently selected from hydrogen and alkyl; and $R^{11}$ is selected from hydrogen, alkyl, alkenyl, alkynyl, cycloalkyl, phenyl, naphthyl, phenylalkyl, acyl and formyl.

14. The compounds of claim 13 wherein Z is —O—.

15. The compounds of claim 13 wherein Z is —S—.

16. The compounds of claim 13 wherein A is a group of formula (II).

17. The compounds of claim 13 wherein A is a group of formula (III).

18. The compounds of claim 13 wherein A is a group of formula (IV).

19. The compounds of claim 14 wherein A is a group of formula (II).

20. The compounds of claim 14 wherein A is a group of formula (III).

21. The compounds of claim 14 wherein A is a group of formula (IV).

22. The compounds of claim 15 wherein A is a group of formula (II).

23. The compounds of claim 15 wherein A is a group of formula (III).

24. The compounds of claim 15 wherein A is a group of formula (IV).

25. The compounds of claim 13 wherein $R^4$, $R^5$, $R^6$, $R^7$, $R^8$ and $R^9$ are selected from hydrogen or methyl.

26. A method of treating a disorder or disease of a living animal body, said disorder or disease selected from the group consisting of an affective disorder, an anxiety disorder, panic disorder and obsessive compulsive disorder, comprising administering to said living animal body a therapeutically effective amount of a compound of claim 13, or a pharmaceutically acceptable acid addition salt thereof.

* * * * *